United States Patent [19]

Lacour et al.

[11] Patent Number: 4,528,380
[45] Date of Patent: Jul. 9, 1985

[54] 5-(1-PROPYL)N-BUTYL TETRAZOLES

[75] Inventors: Alain P. Lacour, La Varenne; Michel Langlois, Buc; Maurice F. Jalfre, Maule; Bernard P. Bucher, Marnes la Coquette, all of France

[73] Assignee: Delalande S.A., France

[21] Appl. No.: 446,971

[22] Filed: Dec. 6, 1982

[30] Foreign Application Priority Data

Dec. 7, 1981 [FR] France ............... 81 22864

[51] Int. Cl.³ .................................... C07D 257/04
[52] U.S. Cl. ........................... 548/250; 514/823
[58] Field of Search ............... 548/250; 424/269

[56] References Cited

PUBLICATIONS

Elderfield, vol. 8, p. 53, (1967), Wiley N.Y., N.Y.

Primary Examiner—Glennon H. Hollrah
Assistant Examiner—D. B. Springer

Attorney, Agent, or Firm—Roylance, Abrams, Berdo & Goodman

[57] ABSTRACT

New tetrazole derivatives, characterized in that they correspond to the formula:

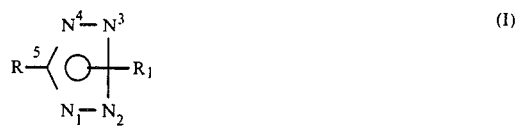

in which $R_1$ represents: either a hydrogen atom in any one of the positions 1 to 5 of the tetrazole nucleus, R designating a branched alkyl group comprising at least 5 carbon atoms or a branched alkenyl group, or a methyl group in position 2(3) of the tetrazole nucleus, R representing the (1-propyl)n butyl chain.

These new derivatives are useful as medicaments, more especially for their anti-epileptic action.

2 Claims, No Drawings

5-(1-PROPYL)N-BUTYL TETRAZOLES

The present invention relates to novel tetrazole derivatives substituted in position 5 by an alkyl or alkenyl group, the process for preparing same and the application thereof in therapeutics.

These new derivatives correspond more precisely to the general formula:

in which $R_1$ represents: either a hydrogen atom in any one of the positions 1 to 5 of the tetrazole nucleus, R designating a branched alkyl group comprising at least 5 carbon atoms or a branched alkenyl group, or a methyl group in position 2(3) of the tetrazole nucleus, R representing the (1-propyl)n butyl chain.

The branched alkyl group comprising at least 5 carbon atoms may in particular be chosen from the following: (1,1-dimethyl)n propyl; (1,1-dimethyl)n butyl; (1-methyl 1-ethyl)n pentyl; (1-propyl 1-methyl)n butyl; (1,1-dipropyl)n butyl; (1-propyl)n butyl; (2-propyl)n pentyl; (1-isopropyl)n butyl.

Moreover, the branched alkenyl group may more particularly be formed by the (2-propen 1-yl)n butyl chain.

When, in formula (I) $R_1$ represents the hydrogen atom, the compounds of the invention are obtained by condensation of the hydrazoate of an alkali metal such as sodium, in the presence of ammonium chloride, in solution in an aprotic solvent such as dimethylformamide, for example in an inert atmosphere (nitrogen or argon), on nitriles of formula:

$$R-CN \quad (II)$$

in which R has the same meanings as in formula (I) when $R_1=H$.

When, in formula (I) $R_1$ represents the methyl group, the compounds of the invention are obtained by the action of methyl iodide, in the presence of sodium hydride, on the compound of formula (I) in which $R_1=H$ and R=(1-propyl)n butyl. This reaction is followed by purification with an appropriate method, particularly fractional distillation, for separating the derivative of formula (I) methylated in position 1 on the tetrazole nucleus, from its isomer methylated in position 2 on the tetrazole nucleus.

The compound of formula (II) in which R represents the (2-propen 1-yl) group is original and is obtained by decarboxylation by heating, preferably at about 200°-220° C., the compound of formula:

The following preparations are given by way of example to illustrate the invention.

EXAMPLE 1

[1-(1-n propyl)n butyl] tetrazole (I)

Code number: 6

A suspension of 1.25 g of 1-cyano (1-n propyl) butane (II), 0.72 g of sodium hydrazoate and 0.6 g of ammonium chloride in 10 ml of DMF is left for 24 hours at 120° C. under argon. Then the solvent is evaporated, the residue is taken up in iced water acidified to pH~2 with 1N hydrochloric acid, the residue obtained is filtered, washed with water on the filter, then with petroleum ether and vacuum dried. Thus 0.5 g of the expected product is obtained.

Melting point: 124° C.
Yield: 29%
Empirical formula: $C_8H_{16}N_4$
Molecular weight: 168.24

| | Elementary analysis: | | |
|---|---|---|---|
| | C | H | N |
| Calculated (%) | 57.11 | 9.59 | 33.30 |
| Obtained (%) | 57.12 | 9.37 | 33.34 |

By the same process, but from the corresponding reagents, the compounds of formula (I) are obtained given under code numbers 1 to 5 and 7 to 9 in Table I below.

EXAMPLE 2

1-cyano 1-(2-propen 1-yl) butane

[(II, R=(CH$_2$=CH—CH$_2$) (nC$_3$H$_7$)CH]

88.6 g of 2-cyano 2-(2-propen 1-yl) pentanoic acid (III) is heated at 200°-220° C. for 2 hours. Then it is distilled to obtain 56 g of the expected product.

Boiling point (under 760 mm Hg)=190° C.
Yield: 86%
Empirical formula: $C_8H_{13}N$
Molecular weight: 123.19

EXAMPLE 3

2-methyl 5-[1-(1-n propyl)n butyl] tetrazole (I)

Code number: 11

To a suspension of 1.7 g of sodium hydride (at 80%) in 50 ml of dioxane is added a solution of 10 g of the compound of formula (I) and code number 6, obtained in example 1, in 100 ml of dioxane. The mixture is heated at 50° C. for 20 minutes, then 5.5 ml of methyl iodide are added drop by drop, and afterwards 60 ml of DMF are added. The obtained mixture is left for 1 hour at 50° C. then thrown into iced water, extracted with ether, washed with water, then with a sodium thiosulfate solution, then with water, dried on sodium sulfate, filtered, the filtrate is evaporated and the residue distilled. Thus 3.5 g of 2-methyl 5-[1-(1-n propyl)n butyl] tetrazole (code number 11) are obtained, whose boiling point under 0.05 mm Hg is 76° C. Furthermore, 4.4 g of 1-methyl 5-[1-(1-n propyl)n butyl] tetrazole are obtained which is distilled at 120° C. under 0.05 mm Hg.

TABLE I

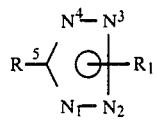
(I)

| Code Number | $R_1$ | R— | Empirical formula | Molecular weight | Melting point (°C.) | | % C | H | N |
|---|---|---|---|---|---|---|---|---|---|
| 1 | H | Et(CH$_3$)$_2$C— | C$_6$H$_{12}$N$_4$ | 140.18 | 166 | Cal. | 51.40 | 8.63 | 39.97 |
| | | | | | | Obt. | 51.71 | 8.85 | 39.92 |
| 2 | " | nC$_3$H$_7$(CH$_3$)$_2$C— | C$_7$H$_{14}$N$_4$ | 154.21 | 134 | Cal. | 54.52 | 9.15 | 36.33 |
| | | | | | | Obt. | 54.56 | 9.45 | 36.55 |
| 3 | " | (nC$_4$H$_9$)(Et)(CH$_3$)C— | C$_9$H$_{18}$N$_4$ | 182.27 | 116 | Cal. | 59.30 | 9.95 | 30.74 |
| | | | | | | Obt. | 59.07 | 9.79 | 30.70 |
| 4 | " | (nC$_3$H$_7$)$_2$(CH$_3$)C— | C$_9$H$_{18}$N$_4$ | " | 154 | Cal. | 59.30 | 9.95 | 30.74 |
| | | | | | | Obt. | 59.08 | 9.92 | 31.03 |
| 5 | " | (nC$_3$H$_7$)$_3$C— | C$_{11}$H$_{22}$N$_4$ | 210.32 | 149 | Cal. | 62.81 | 10.54 | 26.64 |
| | | | | | | Obt. | 63.10 | 10.76 | 26.79 |
| 6 | " | (nC$_3$H$_7$)$_2$CH— | C$_8$H$_{16}$N$_4$ | 168.24 | 124 | Cal. | 57.11 | 9.59 | 33.30 |
| | | | | | | Obt. | 57.12 | 9.37 | 33.34 |
| 7 | " | (nC$_3$H$_7$)$_2$CH—CH$_2$— | C$_9$H$_{18}$N$_4$ | 182.27 | 70 | Cal. | 59.30 | 9.95 | 30.74 |
| | | | | | | Obt. | 58.99 | 9.83 | 30.51 |
| 8 | " | (nC$_3$H$_7$)(isoC$_3$H$_7$)CH— | C$_8$H$_{16}$N$_4$ | 168.24 | 150 | Cal. | 57.11 | 9.59 | 33.30 |
| | | | | | | Obt. | 57.07 | 9.77 | 33.54 |
| 9 | " | CH$_2$=CH—CH$_2$\CH—/nC$_3$H$_7$ | C$_8$H$_{14}$N$_4$ | 166.22 | 106 | Cal. | 57.80 | 8.49 | 33.71 |
| | | | | | | Obt. | 57.90 | 8.67 | 33.51 |
| 11 | 2-CH$_3$ | (nC$_3$H$_7$)$_2$CH— | C$_9$H$_{18}$N$_4$ | 182.27 | Eb$_{0.05}$ = 76° C. | Cal. | 59.30 | 9.95 | 30.74 |
| | | | | | | Obt. | 59.23 | 9.80 | 30.45 |

The compounds of formula (I), tested on laboratoy animals proved to possess pharmacological properties and especially activities in the central nervous system field, in particular anti-convulsive activities.

The anti-convulsive activity was demonstrated on mice by the test of protection against mortality induced by an intravenous injection of 0.7 mg/kg of bicucullin according to the method described by Perez de la Mora in Biochem. Pharmacol. 22, 2635 (1973).

Acute toxicity is assessed intraperitoneally on mice according to the method of Miller and Tainter described in Proc. Soc. Exp. Biol. Med. 57, 261, (1944).

To illustrate the invention a few results obtained in the above tests with compounds of formula (I) are given in table II below.

TABLE II

| Code Number | Acute toxicity LD 50 (mg/kg/i.p.) | ED 50 against mortality induced by bicucullin (mg/kg/i.p.) |
|---|---|---|
| 1 | >400 | 100 |
| 3 | 320 | 120 |
| 5 | 280 | 44 |
| 6 | >400 | 135 |

The difference between the toxic doses and active doses allows the compounds of formula (I) to be used as drugs, particularly in the treatment of troubles of the central nervous system and especially as antiepileptics.

They will be administered preferably in the form of pharmaceutical compositions comprising at least one compound of formula (I), possibly in association with a pharmaceutically acceptable vehicle. For example, they will be administered orally, in the form of tablets, pills or capsules, or in the form of a drinkable aqueous solution, in an amount going up to 3.5 g/day taken in one or more doses, or intravenously or intramuscularly, in the form of injectable ampoules in amounts up to 1.500 mg/day in one or more injections.

We claim:

1. A compound having the formula:

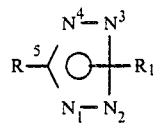

in which $R_1$ represents: either a hydrogen atom in position 1 or 2 of the tetrazole nucleus, R designating a group chosen from the following: (1,1-dimethyl)n-propyl; (1,1-dimethyl)n-butyl; (1-methyl 1-ethyl)n-pentyl; (1-propyl 1-meythyl)n-butyl; (1,1-dipropyl)n-butyl; (1-propyl)n-butyl; (2-propyl)n-pentyl; (1-isopropyl)n-butyl; (2-propen 1-yl)n-butyl; or a methyl group in position 2(3) of the tetrazole nucleus, R representing the (1-propyl)n-butyl chain.

2. A compound as defined in claim 1 wherein $R_1$ is hydrogen and R is (1-propyl)n-butyl.

* * * * *